(12) United States Patent
Murphy

(10) Patent No.: US 6,488,667 B1
(45) Date of Patent: Dec. 3, 2002

(54) NEEDLE CONTROL DEVICE

(76) Inventor: Kieran P. J. Murphy, 119 Beechdale Rd., Baltimore, MD (US) 21210

( * ) Notice: Subject to any disclaimer, the term of this patent is extended or adjusted under 35 U.S.C. 154(b) by 118 days.

(21) Appl. No.: 09/594,151

(22) Filed: Jun. 15, 2000

(51) Int. Cl.[7] ................................................ A61M 5/32
(52) U.S. Cl. ...................................................... 604/272
(58) Field of Search ................................ 604/173, 177, 604/264, 272

(56) References Cited

U.S. PATENT DOCUMENTS

| | | |
|---|---|---|
| 4,177,797 A | 12/1979 | Baylis et al. |
| 4,485,815 A | 12/1984 | Amplatz et al. |
| 4,733,661 A | 3/1988 | Palestrant |
| 4,798,213 A | 1/1989 | Doppelt |
| 5,290,266 A | 3/1994 | Rohling et al. |
| 5,758,655 A | 6/1998 | Como Rodriguez et al. |
| 5,928,238 A | 7/1999 | Scarborough et al. |
| 6,022,324 A | 2/2000 | Skinner |
| 6,033,411 A | 3/2000 | Preissman |

OTHER PUBLICATIONS

Percutaneous Vertebroplasty for Osteolytic Metastases and Myeloma: Effects of the Percentage of Lesion Filling and the Leakage of Methyl Methacrylate at Clinical Follow–up; Anne Cotten, M.D. et al.; Radiology; Aug., 1996; pp. 525–530.

Percutaneous Vertebroplasty: State of the Art; Anne Cotten, M.D. et al; Scientific Exhibit, vol. 18, No. 2, Mar.—Apr. 1998; pp. 311–323.

Primary Examiner—Robert M. Fetsuga
Assistant Examiner—Peter deVore
(74) Attorney, Agent, or Firm—Richard J. Godlewski

(57) ABSTRACT

An apparatus for holding a needle, during exposure to radiation, such as X-ray radiation. The apparatus includes a needle collar and a control bar. The needle collar attaches to needle and has a first attachment point. The control bar has a second attachment point. The first attachment point and the second attachment point cooperate to releasably engage the needle collar and the control bar. In use, the needle collar and the control bar are engaged and the user grasps the control bar to control the needle while maintaining the hands of the user outside of a field of the radiation, e.g., outside of a field of the X-ray radiation. The control bar is dimensioned such that its proximal end (i.e., the end to be grasped by the user) is outside the field of radiation.

27 Claims, 3 Drawing Sheets

NEEDLE CONTROL DEVICE

BACKGROUND OF THE INVENTION

1. Field of the Invention

The present invention relates to a needle control device. More particularly, the present invention relates to a needle control device to obviate or mitigate exposure of excessive radiation to the hand of a user.

2. Description of the Prior Art

Several medical treatments involve the use of needles and continuous applied doses of radiation while a medical practitioner is within the range of the radiation. An example of such a procedure is vertebroplasty.

Percutaneous vertebroplasty involves the injection of a bone cement or other suitable biomaterial into a vertebral body via a percutaneous route under X-ray guidance. The cement is injected as a semi-liquid substance through a needle that has been passed into the vertebral body, generally along a transpedicular or posterolateral approach.

Percutaneous vertebroplasty is intended to provide structural reinforcement of a vertebral body through injection, by a minimally invasive percutaneous approach, of bone cement into the vertebral body. See, for example, Cotton A., et al "Percutaneous vertebroplasty: State of the Art." *Radiograhics* 1998 March–April; 18(2):311–20; discussion at 320–3. Percutaneous vertebroplasty can result in increased structural integrity, decreased micromotion at the fracture site and possibly a destruction of pain fibres due to the heat of the bone cement as it polymerizes and sets. Complete pain relief can be achieved in up to 80% of patients.

Generally, when performing vertebroplasty, a needle of an appropriate gauge (such as 11 gauge or 13 gauge in a smaller vertebral body) is passed down the pedicle until it enters the vertebral body and reaches the junction of the anterior and middle thirds. Great skill is usually required to insert the needle at a suitable angle and pass the needle through the periosteum, down the pedicle and into the vertebral body. A suitable cement is prepared and injected through the needle and into the vertebral body, under lateral X-ray projection fluoroscopy imaging. The injection is stopped as the cement starts to extend into some unwanted location such as the disc space or towards the posterior quarter of the vertebral body, where the risk of epidural venous filling and hence spinal cord compression is greatest. The injection is also discontinued if adequate vertebral filling is achieved.

The procedure usually requires the user (typically a physician) to hold the needle in position while (at least a portion) of the body is being radiated. This is normally needed since the needle should be stabilised and oriented in the correct position in order for the intended target in the body to be reached. This protocol leads to the creation of field of radiation in which the user's hands typically are placed. Consequently, the user will receive repeated doses of radiation which can lead to one or more occupational health hazards (e.g., health problems) and/or can shorten the career of the user due to the user receiving quantities of radiation beyond the allowable limits.

Accordingly, there is a need in the art for a means by which radiative medical procedures such as percutaneous vertebroplasty may be performed while obviating or mitigating to deleterious effects of exposure of the physician or other user to excessive radiation.

SUMMARY OF THE INVENTION

It is an object of the present invention to provide a novel needle control device for holding a needle that obviates or mitigates at least one of the disadvantages of the prior art.

Accordingly, in one of its aspects, the present invention provides an apparatus for control of a needle (i.e., a needle control device) used in a field of radiation, the apparatus comprising:

a needle collar for attachment to the needle, the needle collar comprising a first attachment point; and a control bar having a second attachment point, the first attachment point and the second attachment point cooperating to releasably engage the needle collar and the control bar.

In another of its aspects, the present invention provides a needle comprising:

a handle;

a cannula attached to the handle;

a needle collar attached to the needle, the needle collar comprising a first attachment point; and a control bar having a second attachment point, the first attachment point and the second attachment point cooperating to releasably engage the needle collar and the control bar.

In yet another of its aspects, the present invention provides a kit of parts comprising:

a needle comprising: a handle; a cannula attached to the handle; a needle collar attached to the needle, the needle collar comprising a first attachment point; and a control bar having a second attachment point, the first attachment point and the second attachment point cooperating to releasably engage the needle collar and the control bar.

Thus, the present inventor has developed an apparatus for holding a needle, during exposure to radiation, such as X-ray radiation. The apparatus includes a needle collar and a control bar. The needle collar attaches to needle and has a first attachment point. The control bar has a second attachment point. The first attachment point and the second attachment point cooperate to releasably engage the needle collar and the control bar. In use, the needle collar and the control bar are engaged and the user grasps the control bar to control the needle while maintaining the hands of the user outside of a field of the radiation, e.g., outside of a field of the X-ray radiation. The control bar is dimensioned such that its proximal end (i.e., the end to be grasped by the user) is outside the field of radiation.

BRIEF DESCRIPTION OF THE DRAWINGS

Embodiments of the present invention will be described with reference to the accompanying drawings, in which.

DETAILED DESCRIPTION OF THE PREFERRED EMBODIMENTS

Before discussing the presently preferred embodiment of the invention, a needle suitable for use with the needle control device will be described with reference to FIG. 1.

Figure 1:
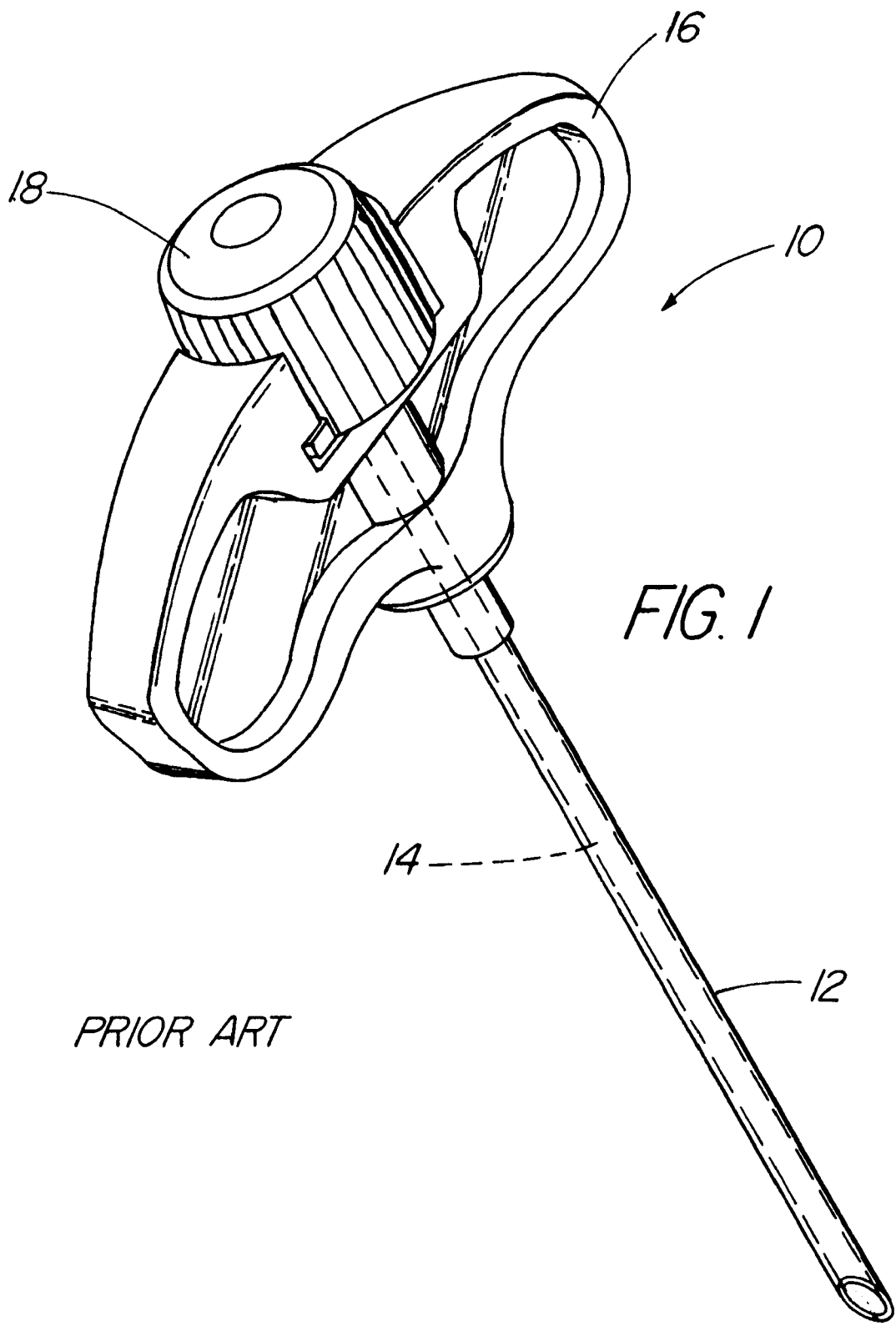
FIG. 1 illustrates a perspective view of conventional a vertebroplasty needle.

Thus, with reference to FIG. 1, a vertebroplasty needle is indicated generally at 10. Needle 10 is preferably used for expressing bone cement or a suitable biomaterial into a vertebral body. In a presently preferred embodiment, needle 10 is constructed of surgical stainless steel. Those of skill in the art will appreciate that needle 10 may be constructed of any other suitable materials can be used, as will occur to those of skill in the art. Vertebroplasty needle 10 generally consists of a cannula (also referred to as a sheath or a trocar) 12 and an insert 14 receivably removable with in the sheath. Cannula 12 has a handle 16 for grasping by an operator. Insert 14 has a connector 18 operable to releasably attach to handle 16. Insert 14 is receivable within cannula 12 for insertion of needle 10 into a vertebral body via percutaneous routes. Insert 14 is removable from cannula 12 to allow for a conventional injector (not shown), suitable for cement delivery, to be releasably attached to handle 16 to facilitate the injection of cement through cannula 12 into a vertebral body. The injector can be a syringe or a cement delivery needle or other suitable injectors as will occur to those of skill in the art.

Figure 2:
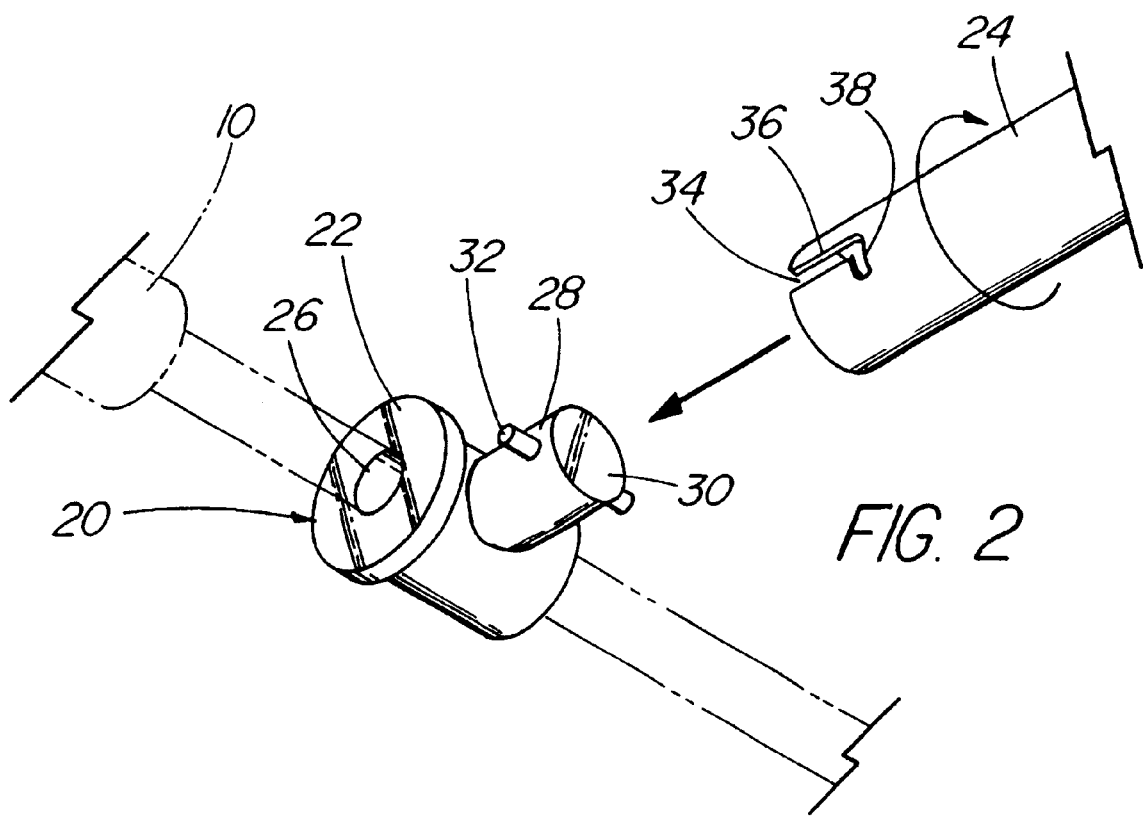
FIG. 2 illustrates a perspective view of a portion of the present needle control device with the control bar removed.
Figure 3:
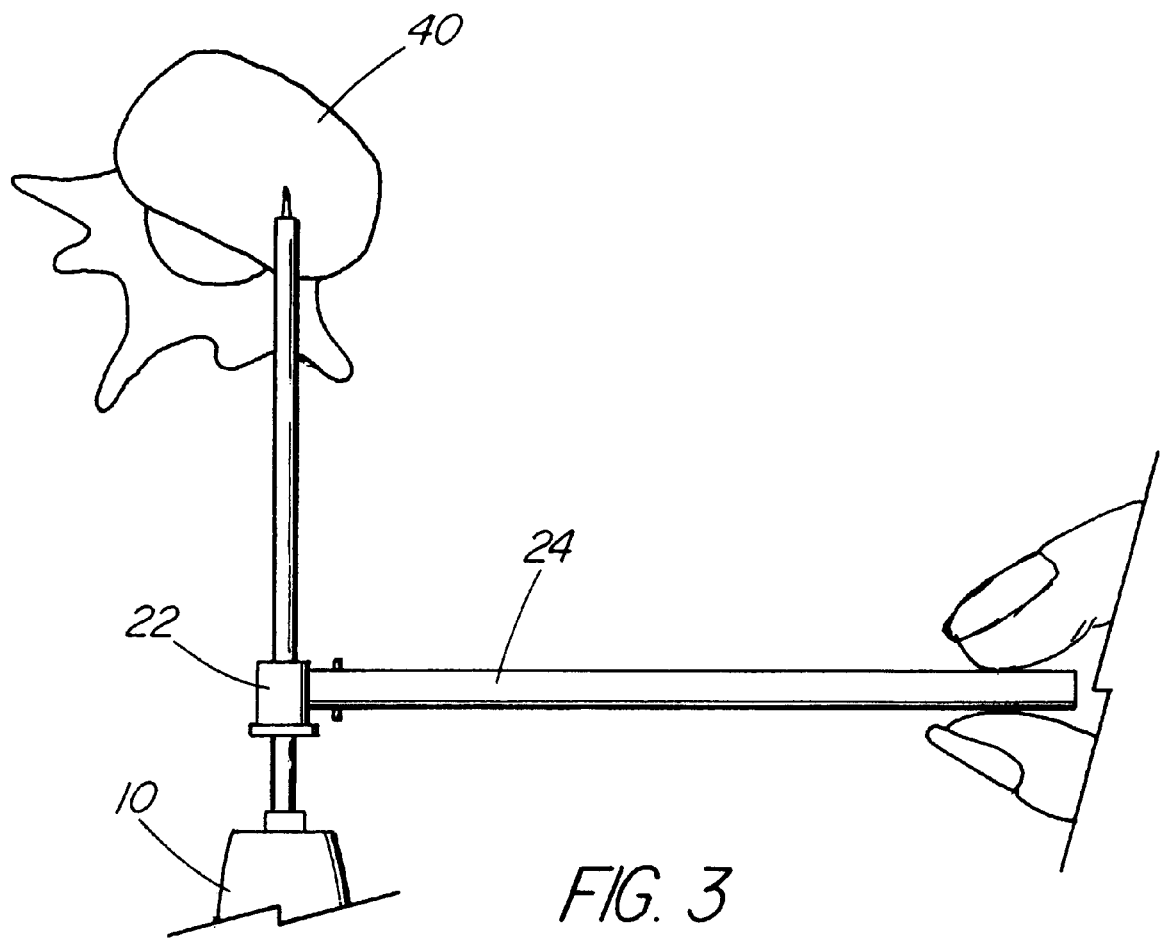
FIG. 3 illustrate a perspective schematic view of the present needle control device in use.

Referring now to FIGS. 2–3, a needle control device for holding a needle is indicated generally at 20. Device 20 includes a needle collar 22 that is releasably attachable to a control bar 24.

In a presently preferred embodiment, needle collar 22 has an opening 26 for releasably engaging with needle 10 when needle 10 is passed through opening 26. In a presently preferred embodiment needle collar 22 is a depth marker and is made from medical grade plastic or from other suitable materials. Other embodiments of needle collar 22 will occur to those of skill in the art, such as depth markers that include a gasket which can be constricted or loosened about the needle in order to adjust the grip of the depth marker on the needle. The interior diameter of opening 26 in needle collar 22 is slightly larger than the exterior diameter of needle 10, and the size and material of needle collar 22 cooperates to create a friction or interference fit around needle 10. Other suitable depth markers can be used, as will occur to those of skill in the art.

Needle collar 22 has a first attachment point 28. First attachment point 28 protrudes from needle collar 22 and is operable to connect with control bar 24. In a presently preferred embodiment, first attachment point 28 comprises a post 30 with a pair of bosses 32 substantially perpendicular to post 30.

Control bar 24 is made from medical grade plastic or other suitable materials can be used, as will occur to those of skill in the art. Preferably, control bar 24 is radiolucent, so as not to interfere with the X-ray image. Control bar 24 is operable to connect with first attachment point 28. In a presently preferred embodiment, control bar 24 has a second attachment point 34 that releasably engages with first attachment point 28. Second attachment point 34 has a pair of slots 36 and a pair of recesses 38, respective to slots 36. Recesses 38 are substantially perpendicular to each slot 36 to releasably retain a respective boss 32. Recesses 38 extend substantially in opposite directions, so that when control bar 24 is twisted each boss 32 is received and retained with in its respective slot 36.

Preferably, control bar 24 is from about 10 to about 40 cm in length. More preferably, control bar 24 is from about 20 to about 30 cm. It will be understood by those skilled in the art, however, that the length of control bar 24 may vary depending on the size of the needle that is used and the medical process it is being used in. In particular, the length of control bar 24 is chosen to ensure that it can be grasped in a position that is outside the field of radiation generated during the procedure.

The operation of device 20 will now be described with reference to the foregoing and to attached FIG. 3. More specifically, a method for performing vertebroplasty in accordance with an embodiment of the invention will now be discussed, utilizing needle 10 and needle control device 20 and performed on a patient having a vertebrae 40. Referring now to FIG. 3, the patient is placed in the prone position so that vertebrae 40 is within the radiation field generated by an imaging device. In most such cases, the imaging device is an X-ray projection fluoroscopy imaging device.

Needle 10 is inserted into the vertebral body of the patient. Bar 24 is attached to needle 10 by engaging bosses 32 in slots 36 and rotating control bar 24 until bosses 32 are releasably engaged in recesses 38. Control bar 24 is oriented to position the user's hand outside of the field of X-ray radiation. Control bar 24 is grasped by the user and the X-ray device is turned on and an image is taken. The X-ray only exposes the vertebral body, the needle and the needle control device.

While the embodiments discussed herein are directed to particular implementations of the present invention, it will be apparent that variations to these embodiments are within the scope of the invention. For example, needle control device 20 can be made from any material that is suitable for surgical procedures and is radiolucent.

Further, it is contemplated that first attachment point 28 can be a male luer lock and second attachment point 34 can be a female luer lock (or vice versa). Alternatively first attachment point 28 can be a male luer slip and second attachment point 34 can be a female luer slip (or vice versa).

The present invention provides a novel needle control device for holding a needle during exposure to radiation, such as X-ray radiation. Of course, those of skill in the art will recognize that present needle control device has a number of applications and uses in image guided procedures (e.g., magnetic resonance imaging (MRI) and the like)The device includes a needle collar for retaining the needle and a control bar for allowing the user to hold the needle in position prior to and/or during and/or after the X-ray process. The needle collar includes a first attachment point that, preferably, is complimentary to a second attachment point positioned on the bar for releasable attachment to the control bar. The control bar allows the user to maintain control over the needle while taking an X-ray image and avoid exposing the user to the excessive X-ray radiation.

While the present invention has been described with reference to preferred and specifically illustrated embodiments, it will of course be understood by those skilled in the arts that various modifications to these preferred and illustrated embodiments may be made without departing from the spirit and scope of the invention.

All publications, patents and patent applications referred to herein are incorporated by reference in their entirety to the same extent as if each individual publication, patent or patent application was specifically and individually indicated to be incorporated by reference in its entirety.

What is claimed is:

1. An apparatus for control of a needle cannula used in a field of radiation, the apparatus comprising:
    a needle collar for attachment to the needle cannula, the needle collar comprising a first attachment point; and
    a control bar having a second attachment point, the first attachment point and the second attachment point cooperating to releasably engage the needle collar and the control bar.

2. The apparatus defined in claim 1, wherein the needle collar comprises an annular section to receive the needle cannula.

3. The apparatus defined in claim 1, wherein the needle collar comprises a sleeve section to receive the needle cannula.

4. The apparatus defined in claim 1, wherein the first attachment point comprises a male member and the second attachment point comprises a female member.

5. The apparatus defined in claim 1, wherein the first attachment point comprises a male luer lock and the second attachment point comprises a female luer lock.

6. The apparatus defined in claim 1, wherein the first attachment point comprises a male luer slip and the second attachment point comprises a female luer slip.

7. The apparatus defined in claim 1, wherein the first attachment point comprises a post including a pair of bosses and the second attachment point having a pair of slots and a pair of recesses extending angularly from the slots to receive the bosses therein.

8. The apparatus defined in claim 1, wherein the needle collar comprises a depth marker.

9. The apparatus defined in claim 1, wherein the needle collar comprises a gasket.

10. The apparatus defined in claim 1, wherein the control bar is constructed of a radiolucent material.

11. The apparatus defined in claim 1, wherein the control bar comprises a longitudinal member having a length in the range of from about 10 to about 40 cm.

12. The apparatus defined in claim 1, wherein the control bar comprises a longitudinal member having a length in the range of from about 20 to about 30 cm.

13. The apparatus defined in claim 1, wherein the needle collar and the control bar are releasably engagable in a substantially perpendicular orientation.

14. A needle comprising:
   a handle;
   a cannula attached to the handle;
   a needle collar attached to the cannula the needle collar comprising a first attachment point; and
   a control bar having a second attachment point, the first attachment point and the second attachment point cooperating to releasably engage the needle collar and the control bar.

15. The needle defined in claim 14, wherein the needle collar and the control bar are releasably engagable in a substantially perpendicular orientation.

16. The needle defined in claim 14, wherein the needle collar comprises an annular section to receive the cannula.

17. The needle defined in claim 14, wherein the needle collar comprises a sleeve section to receive the cannula.

18. The needle defined in claim 14, wherein the first attachment point comprises a male member and the second attachment point comprises a female member.

19. The needle defined in claim 14, wherein the first attachment point comprises a male luer lock and the second attachment point comprises a female luer lock.

20. The needle defined in claim 14, wherein the first attachment point comprises a male luer slip and the second attachment point comprises a female luer slip.

21. The needle defined in claim 14, wherein the first attachment point comprises a post including a pair of bosses and the second attachment point having a pair of slots and a pair of recesses extending angularly from the slots to receive the bosses therein.

22. The needle defined in claim 14, wherein the needle collar comprises a depth marker.

23. The needle defined in claim 14, wherein the needle collar comprises a gasket which is pierceable by the cannula to create an interference fit therebetween.

24. The needle defined in claim 14, wherein the control bar is constructed of a radiolucent material.

25. The needle defined in claim 14, wherein the control bar comprises a longitudinal member having a length in the range of from about 10 to about 40 cm.

26. The needle defined in claim 14, wherein the control bar comprises a longitudinal member having a length in the range of from about 20 to about 30 cm.

27. A kit of parts comprising:
   a needle comprising: a handle; a cannula attached to the handle; a needle collar attached to the cannula, the needle collar comprising a first attachment point; and
   a control bar having a second attachment point, the first attachment point and the second attachment point cooperating to releasably engage the needle collar and the control bar.

* * * * *